United States Patent [19]

Grohe et al.

[11] Patent Number: 4,762,844

[45] Date of Patent: Aug. 9, 1988

[54] ANTIBACTERIALLY ACTIVE ALKYL-1-CYCLOPROPYL-1,4-DIHYDRO-4-OXO-3-QUINOLINECARBOXYLIC ACIDS

[75] Inventors: Klaus Grohe, Odenthal; Michael Schriewer, Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 795,056

[22] Filed: Nov. 5, 1985

[30] Foreign Application Priority Data

Nov. 15, 1984 [DE] Fed. Rep. of Germany ....... 3441788

[51] Int. Cl.[4] .................... A61K 31/47; C07D 215/56
[52] U.S. Cl. .................................. 514/312; 546/156; 260/544 D; 560/23; 560/53; 560/54; 560/48
[58] Field of Search .......................... 546/156; 514/312

[56] References Cited

U.S. PATENT DOCUMENTS

| | | | |
|---|---|---|---|
| 3,849,421 | 11/1974 | Nakagome et al. | 546/156 X |
| 4,327,101 | 4/1982 | Mushika et al. | 514/312 |
| 4,544,747 | 10/1985 | Ishikawa et al. | 546/156 |
| 4,556,658 | 12/1985 | Grohe et al. | 514/254 |
| 4,563,459 | 1/1986 | Grohe et al. | 514/312 X |
| 4,571,396 | 2/1986 | Hutt et al. | 546/156 X |
| 4,623,650 | 11/1986 | Gilligan et al. | 514/312 |

FOREIGN PATENT DOCUMENTS 2246503 4/1974 Fed. Rep. of Germany ...... 546/156
3248507 7/1984 Fed. Rep. of Germany ...... 514/312

OTHER PUBLICATIONS

Wise, et al., Antimicrobial Agents and Chemotherapy, vol. 23, No. 4, pp. 559-564 (04/83).

Primary Examiner—Robert Gerstl
Assistant Examiner—Diana G. Rivers
Attorney, Agent, or Firm—Sprung Horn Kramer & Woods

[57] ABSTRACT

Alkyl-1-cyclopropyl-1,4-dihydro-4-oxo-3-quinolinecarboxylic acids of the formula

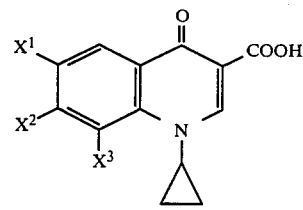

in which $X^1$, $X^2$ and $X^3$ each independently is hydrogen, a nitro group, a halogen atom or an alkyl radical with 1 to 3 carbon atoms, with the proviso that at least one of them is an alkyl radical, or pharmaceutically acceptable salts or hydrates thereof, are antibacterially active and promote animal growth.

13 Claims, No Drawings

ANTIBACTERIALLY ACTIVE ALKYL-1-CYCLOPROPYL-1,4-DIHYDRO-4-OXO-3-QUINOLINECARBOXYLIC ACIDS

The invention relates to new alkyl-1-cyclopropyl-1,4-dihydro-4-oxo-3-quinolinecarboxylic acids, a process for their preparation and antibacterial agents containing these compounds, and their use in combating diseases.

7-Amino-1-cyclopropyl-4-oxo-1,4-dihydro-naphthyridine-3-carboxylic acids and 1-cyclopropyl-6-fluoro-1,4-dihydro-4-oxo-7-piperazino-quinoline-3-carboxylic acids and their use as antibacterial agents are known from U.S. Ser. No. 436,112, filed 10/22/82, and U.S. Ser. No. 292,560, filed 8/13/81, both abandoned.

The new alkyl-1-cyclopropyl-1,4-dihydro-4-oxo-3-quinolinecarboxylic acids of the formula I

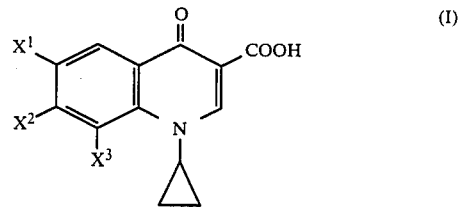

in which $X^1$, $X^2$ and $X^3$ denote hydrogen and/or an alkyl radical with 1 to 3 carbon atoms, with the proviso that at least one radical $X^1$, $X^2$ or $X^3$ represents an alkyl radical, and $X^1$, $X^2$ and $X^3$ can furthermore be the nitro group or a halogen atom, preferably fluorine or chlorine, and pharmaceutically usable salts thereof, have now been found.

The compounds of the formula I are suitable as active compounds in human and veterinary medicine, veterinary medicine also including the preventive treatment of fish.

The alkyl-1-cyclopropyl-1,4-dihydro-4-oxo-3-quinolinecarboxylic acids I can be prepared in accordance with the following equation:

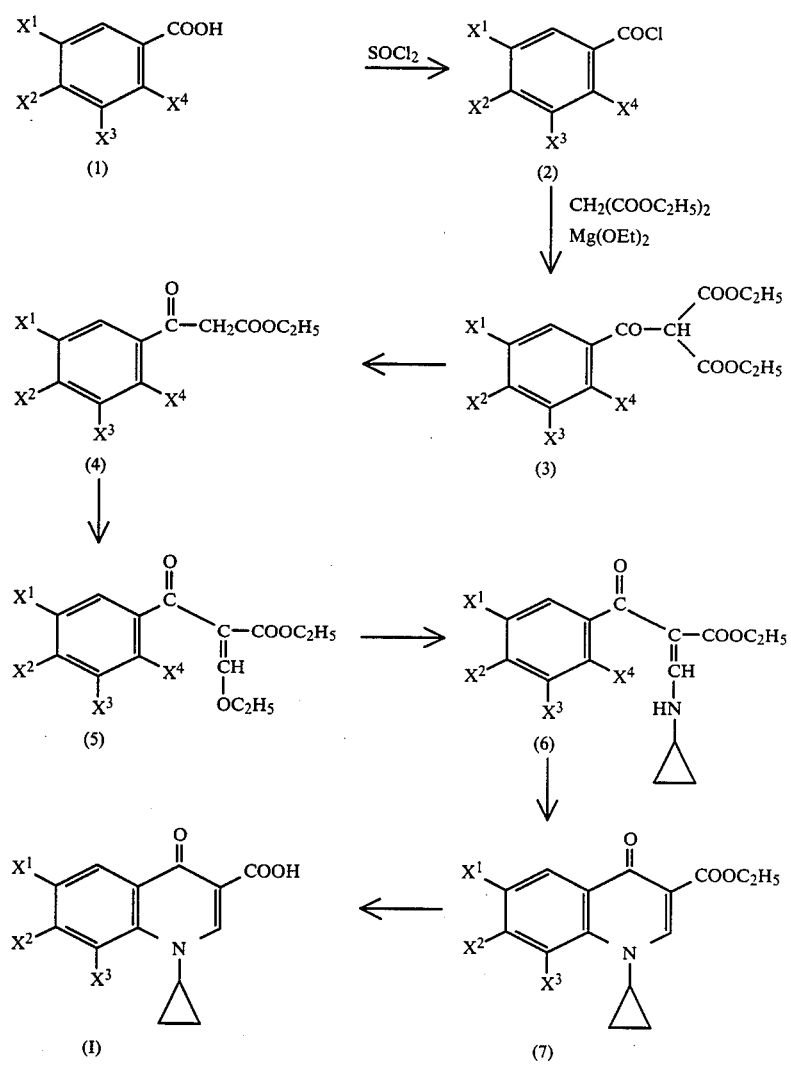

wherein $X^4$ denotes halogen, preferably chlorine or fluorine, or nitro.

According to this equation, diethyl malonate is acylated with the substituted benzoyl halide (2) in the presence of magnesium ethylate to give the aroylmalonate (3) (Organicum, 3rd edition 1964, page 438).

Partial hydrolysis and decarboxylation of (3) in an aqueous medium with catalytic amounts of sulphuric acid or p-toluenesulphonic acid gives a good yield of the ethyl aroylacetate (4), which is converted into the substituted ethyl 3-ethoxyacrylate (5) with triethyl o-formate/acetic anhydride. The reaction of (5) with cyclopropylamine in a solvent, such as, for example, methylene chloride, ethyl alcohol, chloroform, cyclohexane or toluene, gives the desired intermediate product (6) in a slightly exothermic reaction.

The cyclization reaction (6)–(7) is carried out in a temperature range from about 60° to 300° C., preferably 80° to 180° C.

Diluents which can be used for the cyclization reaction are dimethylsulphoxide, N-methylpyrrolidone, sulpholane, hexamethylphosphoric acid triamide and, preferably, N,N-dimethylformamide.

Possible acid-binding agents for this reaction stage are potassium tert.-butanolate, butyl-lithium, lithium-phenyl, phenyl-magnesium bromide, sodium methylate, sodium hydride and, particularly preferably, potassium carbonate or sodium carbonate. It may be advantageous here to use an excess of 10 mol % of base.

The ester hydrolysis of (7) which takes place in the last step under basic or acid conditions leads to the alkyl-1-cyclopropyl-1,4-dihydro-4-oxo-3-quinolinecarboxylic acids (I).

The invention accordingly also relates to a process for the preparation of alkyl-1-cyclopropyl-1,4-dihydro-4-oxo-3-quinolinecarboxylic acids of the formula I

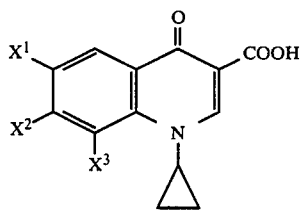

(I)

which is characterized in that substituted benzoic acids of the formula (1)

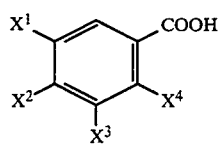

(1)

in which
$X^4$ represents nitro or halogen, preferably chlorine or fluorine, and
$X^1$, $X^2$ and $X^3$ have the abovementioned meaning,
are converted into the corresponding acid halide of the formula (2)

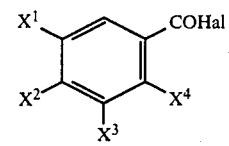

(2)

wherein
$X^1$, $X^2$, $X^3$ and $X^4$ are as defined above and
Hal represents halogen, preferably Cl,
for example by reaction with $SOCl_2$, Diethyl malonate is acylated with the substituted benzoyl halide (2) in the presence of magnesium methylate to give the aroylmalonate of the formula (3)

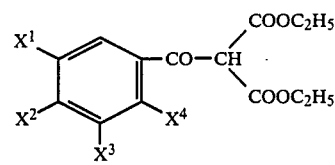

(3)

wherein $X^1$, $X^2$, $X^3$ and $X^4$ are again as defined above, the aroylmalonate (3) is converted into the ethyl aroylacetate (4)

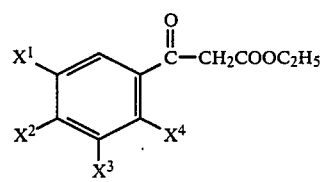

(4)

wherein $X^1$, $X^2$, $X^3$ and $X^4$ are again defined as above, by partial hydrolysis and decarboxylation in an aqueous medium with catalytic amounts of sulphuric acid or p-toluenesulphonic acid, the ethyl aroylacetate is reacted with triethyl o-formate/acetic anhydride to give the substituted ethyl 3-ethoxy-acrylate (5)

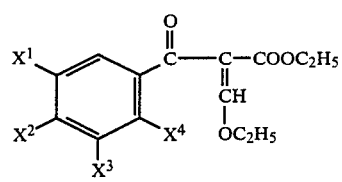

(5)

in which the substituents are as defined above, the reaction product (5) is converted into the intermediate product (6)

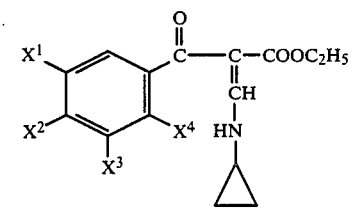

(6)

in which the substituents are as defined above, with cyclopropylamine in a solvent, such as methylene chloride, alcohol, chloroform, cyclohexane or toluene, the intermediate product is cyclized at temperatures of 60° to 300° C. to give the compound (7)

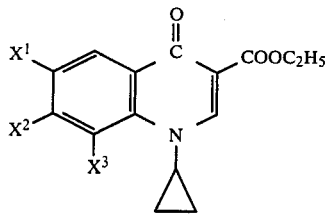

and, finally, the compound (7) is hydrolized to give compounds of the formula (I).

If 2-chloro-3,5-difluoro-4-methylbenzoic acid is used as the starting substance, the course of the reaction can be represented by the following equation:

The syntheses of the new benzoyl halides are described in the experimental part.

New active compounds which may be mentioned specifically are: 1-cyclopropyl-6,8-difluoro-7-methyl-1,4-dihydro-4-oxo-3-quinolinecarboxylic acid, 1-cyclopropyl-6-fluoro-7-methyl-1,4-dihydro-4-oxo-3-quinolinecarboxylic acid, 6-chloro-1-cyclopropyl-7-methyl-1,4-dihydro-4-oxo-3-quinolinecarboxylic acid, 7-chloro-1-cyclopropyl-8-methyl-1,4-dihydro-4-oxo-3-quinolinecarboxylic acid, 8-chloro-1-cyclopropyl-6-fluoro-7-methyl-1,4-dihydro-4-oxo-3-quinolinecarboxylic acid, 6-chloro-1-cyclopropyl-8-fluoro-7-methyl-1,4-dihydro-4-oxo-3-quinolinecarboxylic acid, 7-chloro-1-cyclopropyl-6-fluoro-8-methyl-1,4-dihydro-4-oxo-3-quinolinecarboxylic acid, 1-cyclopropyl-6-fluoro-7-

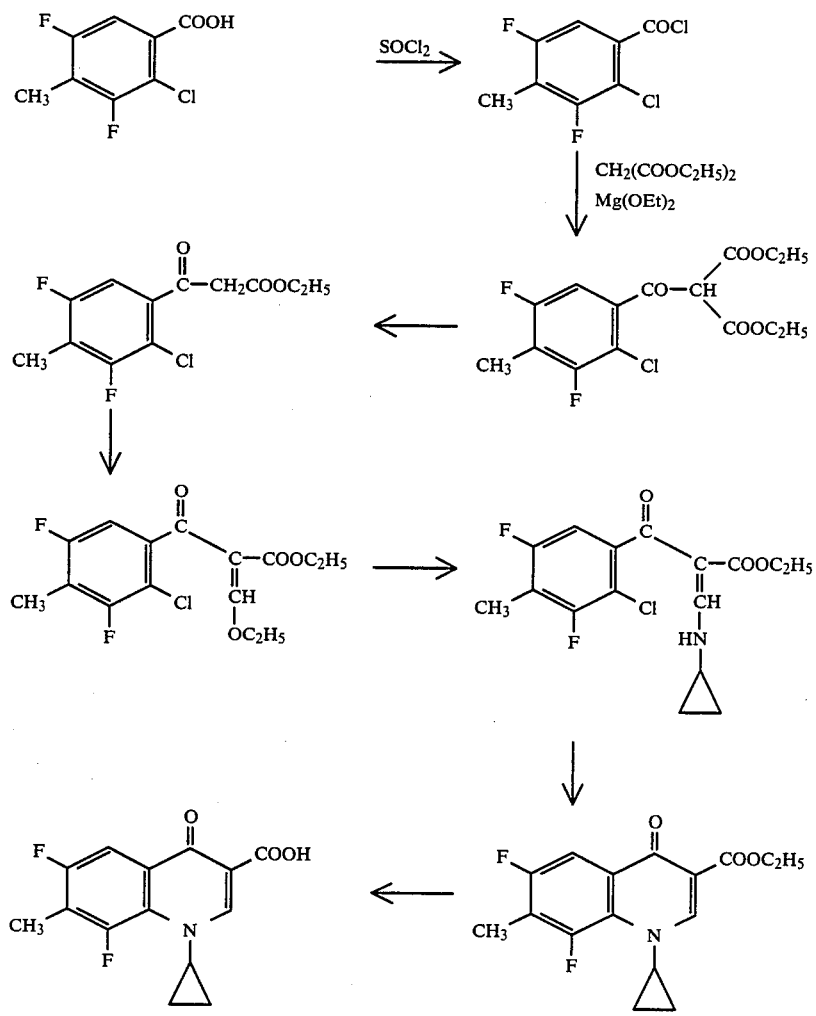

The following benzoyl halides used as starting materials or the corresponding benzoic acids are described in the literature: 2,5-dichloro-4-methylbenzoyl chloride, 5-bromo-2-chloro-4-methylbenzoyl chloride, 2-chloro-3,5-dinitro-4-methylbenzoyl chloride, 2,4-dinitro-5-methylbenzoyl chloride, 2,5-dichloro-4-methyl-3-nitrobenzoyl chloride, 2,4-dichloro-3-methylbenzoyl chloride, 2,4-dichloro-5-methylbenzoyl chloride, 2-chloro-4,5-dimethylbenzoyl chloride and 2-chloro-4-methyl-5-nitrobenzoyl chloride.

methyl-8-nitro-1,4-dihydro-4-oxo-3-quinolinecarboxylic acid, 1-cyclopropyl-7-methyl-6,8-dinitro-1,4-dihydro-4-oxo-3-quinolinecarboxylic acid, 1-cyclopropyl-6-methyl-7-nitro-1,4-dihydro-4-oxo-3-quinolinecarboxylic acid, 6-chloro-1-cyclopropyl-7-methyl-8-nitro-1,4-dihydro-4-oxo-3-quinolinecarboxylic acid, 7-chloro-1-cyclopropyl-6-methyl-1,4-dihydro-4-oxo-3-quinolinecarboxylic acid, 1-cyclopropyl-6,7-dimethyl-1,4-dihydro-4-oxo-3-quinolinecarboxylic acid, 1-cyclopropyl-6,7-dimethyl-8-nitro-1,4-dihydro-4-oxo-3-quinolinecarboxylic acid and 1-cyclopropyl-7-methyl-6-nitro-1,4-dihydro-4-oxo-3-quinolinecarboxylic acid and their pharmaceutically usable alkali metal salts, alkaline earth metal salts or hydrates.

The compounds according to the invention have outstanding antimicrobial properties.

In particular, they have a broad bacteriostatic and bactericidal action against Gram-positive bacteria, such as Straphylococci and Streptococci, and Gram-negative bacteria, such as Escherichia, Proteus, Providencia, Enterobacter, Klebsiella, Salmonella and Pseudomonas. The listing of these sensitive bacteria is to be regarded as by way of example and in no way limiting.

The improved broad antibacterial activity of the compounds according to the invention enables them to be used as active compounds both in human medicine and in veterinary medicine, where they can be used both for the prevention and for the treatment of systemic or local bacterial infections, in particular of the urinary tract. The compounds according to the invention can furthermore be used as feed additives for promoting growth and for improving feed utilization in animal husbandry, in particular in the rearing of fattening animals. The active compounds are then preferably administered by the feed and/or the drinking water.

The present invention furthermore relates to agents which contains the new compounds according to the invention and the preparation of these agents. These include, for example, feed concentrates for animal husbandry, which, besides the active compounds, can also contain vitamins and/or mineral salts in the customary manner, or pharmaceutical formulations.

The invention preferably relates to antibacterial active agents which contain compounds of the formula I. The invention particularly preferably relates to those antibacterially active agents which contain compounds of the formula I or alkali metal or alkaline eath metal salts thereof.

Besides the new compounds according to the invention, the pharmaceutical formulations according to the invention contain non-toxic, inert pharmaceutically suitable excipients in the customary manner. Examples of such pharmaceutically suitable excipients are fillers and extenders, binders, humectants, solution retarders, absorption accelerators, wetting agents, adsorbents or lubricants, which can have a solid, semi-solid or liquid consistency. Such pharmaceutically suitable excipients are known to the expert.

Tablets, dragees, capsules, pills, granules, suppositories, solutions, suspensions and emulsions, pastes, ointments, gels, creams, lotions, powders and sprays may be mentioned as preferred pharmaceutical formulations. These formulations are prepared by known methods in the customary manner, for example by mixing the new active compound according to the invention with the customary excipients and additives. The active compound should be present in the pharmaceutical formulations mentioned in a concentration of about 0.1 to 99.5, preferably about 0.5 to 95% by weight of the total mixture.

The provision of new bactericides for combating bacteria which are resistant towards known bactericides is an enrichment of the state of the art.

The activity of some active compounds according to the invention in the MIC test is demonstrated in the following table.

TABLE 1

| | Example No. | | | |
|---|---|---|---|---|
| | 1 | 2 | 12 | 6 |
| E. coli 4418 | 0.06 | ≦0.015 | ≦0.015 | ≦0.015 |
| E. coli Neumann | ≦0.015 | ≦0.015 | ≦0.015 | ≦0.015 |
| E. coli A261 | 0.06 | 0.015 | ≦0.015 | ≦0.015 |
| Klebsiella pneum. 63 | 0.25 | 0.125 | 0.03 | 0.03 |
| Klebsiella pneum. 8085 | 0.06 | ≦0.015 | 0.03 | ≦0.015 |
| Proteus vulgar. 1017 | 0.25 | ≦0.015 | 0.06 | ≦0.015 |
| Providencia stuartii 12012 | 0.25 | 0.03 | 0.06 | 0.03 |
| Staphylococcus aureus 133 | 0.25 | 2 | 0.125 | ≦0.015 |
| Staphylococcus aureus 1756 | 0.5 | 2 | 0.125 | ≦0.015 |
| Pseudomonas aeruginosa W. | 4 | 8 | 2 | 1 |

Agar dilution test: Isosensitest medium
Denley Multipoint inoculator

PREPARATION EXAMPLES

Example 1

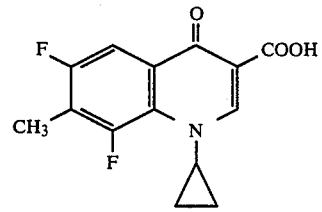

4.5 g of magnesium chips are suspended in 10 ml of anhydrous ethanol. 1 ml of carbon tetrachloride is added and, when the reaction has started, a mixture of 29.7 g of diethyl malonate, 20 ml of absolute ethanol and 80 ml of anhydrous toluene is added dropwise at 50°-60° C. The mixture is then heated at 50°-60° C. for a further hour and cooled to −5° C. to −10° C. with dry ice/acetone and a solution of 41.7 g of 2-chloro-3,5-difluoro-4-methylbenzoyl chloride in 20 ml of absolute toluene is slowly added dropwise at this temperature. The mixture is stirred at 0° to −5° C. for 1 hour and left to come to room temperature overnight, and a mixture of 80 ml of ice-water and 12 ml of concentrated sulphuric acid is allowed to run in, while cooling with ice. The phases are separated and subsequently extracted twice with toluene. The combined toluene solutions are washed with saturated NaCl solution and dried with $Na_2SO_4$ and the solvent is stripped off in vacuo. 65.1 g of diethyl 2-chloro-3,5-difluoro-4-methylbenzoyl-malonate are obtained as a crude product.

0.1 g of p-toluenesulphonic acid is added to an emulsion of 65.1 g of crude diethyl 2-chloro-3,5-difluoro-4-methyl-benzoyl-malonate in 70 ml of water. The mixture is heated to the boiling point for 4.5 hours, with thorough stirring, the cooled emulsion is extracted several times with methylene chloride, the combined $CH_2Cl_2$ solutions are washed once with saturated NaCl solution and dried with $Na_2SO_4$ and the solvent is distilled off in vacuo. Fractionation of the residue under a fine vacuum gives 33 g of ethyl 2-chloro-3,5-difluoro-4-methylbenzoyl-acetate of boiling point 108°-118° C./0.09 mbar.

A mixture of 32.5 g of ethyl 2-chloro-3,5-difluoro-4-methylbenzoyl-acetate, 26.7 g of ethyl o-formate and 30.6 g of acetic anhydride is heated at 150° C. for 2 hours. The volatile constituents are then distilled off under a waterpump vacuum, and finally under a fine vacuum, at a bath temperature of 120° C. 38.6 g of crude ethyl 2-(2-chloro-3,5-difluoro-4-methyl-benzoyl)-3- ethoxyacrylate remain. This compound is sufficiently pure for the subsequent reactions.

7.4 g of cyclopropylamine are added dropwise to a solution of 38.7 g of ethyl 2-(2-chloro-3,5-difluoro-4-methylbenzoyl)-3-ethoxyacrylate in 100 ml of ethanol, while cooling with ice and stirring. When the exothermic reaction has subsided, the mixture is stirred at room temperature for a further ½ hour, 110 ml of water are added and the precipitate is filtered off cold with suction and dried in vacuo. 38.2 g of ethyl 2-(2-chloro-3,5-difluoro-4-methylbenzoyl)-3-cyclopropyl amino-acrylate of melting point 121°–122° C. are obtained.

16.5 g of potassium carbonate are added to a solution of 37.7 g of ethyl 2-(2-chloro-3,5-difluoro-4-methylbenzoyl)-3-cyclopropylamino-acrylate in 100 ml of anhydrous dimethylformamide. The reaction mixture is then stirred under reflux for 2 hours and poured hot onto ice. The precipitate is filtered off with suction, washed thoroughly with water and dried in vacuo over calcium chloride at 100° C. 30.4 g of ethyl 1-cyclopropyl-6,8-difluoro-7-methyl-1,4-dihydro-4-oxo-3-quinolinecarboxylate of melting point 177°–179° C. are obtained.

A mixture of 30 g of ethyl 1-cyclopropyl-6,8-difluoro-7-methyl-1,4-dihydro-4-oxo-3-quinolinecarboxylate, 210 ml of glacial acetic acid, 160 ml of water and 23.5 ml of concentrated sulphuric acid is heated under reflux for 2 hours. The hot suspension is then poured onto ice and the precipitate is filtered off with suction, rinsed thoroughly with water and dried in vacuo at 100° C. 25.9 g of pure 1-cyclopropyl-6,8-difluoro-7-methyl-1,4-dihydro-4-oxo-3-quinolinecarboxylic acid of melting point 227°–229° C. are obtained in this manner.

EXAMPLE 2

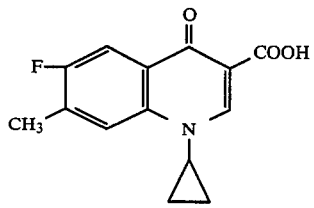

Analogously to Example 1, starting from 2,5-difluoro-4-methyl-benzoyl chloride, comparable yields of ethyl 2,5-difluoro-4-methyl-benzoyl-acetate of boiling point 120°–130° C./0.09 mbar, ethyl 2-(2,5-difluoro-4-methyl-benzoyl)-3-cyclopropylamino-acrylate of melting point 65°–67° C., ethyl 1-cyclopropyl-6-fluoro-7-methyl-1,4-dihydro-4-oxo-3-quinolinecarboxylate of melting point 221°–223° C. and 1-cyclopropyl-6-fluoro-7-methyl-1,4-dihydro-4-oxo-3-quinoline-3-carboxylic acid of melting point 246°–248° C. are obtained.

The following ethyl 2-benzoyl-3-cyclopropylaminoacrylates were obtained analogously to Example 1:

TABLE 2

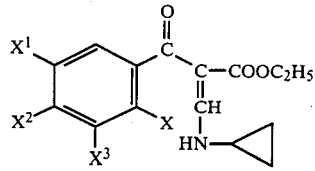

| $X^1$ | $X^2$ | $X^3$ | X | Melting point (°C.) |
|---|---|---|---|---|
| Cl | $CH_3$ | H | Cl | 108–110 |

TABLE 2-continued

| $X^1$ | $X^2$ | $X^3$ | X | Melting point (°C.) |
|---|---|---|---|---|
| Br | $CH_3$ | H | Cl | 102–105 |
| Cl | $CH_3$ | F | Cl | 99–101 |
| F | $CH_3$ | Cl | Cl | 105–107 |
| F | Cl | $CH_3$ | Cl | 108–110 |
| F | $CH_3$ | $NO_2$ | Cl | 156–157 |
| $NO_2$ | $CH_3$ | $NO_2$ | Cl | 153–155 |
| $CH_3$ | $NO_2$ | H | $NO_2$ | 70–75 |
| Cl | $CH_3$ | $NO_2$ | Cl | 144–148 |
| H | Cl | $CH_3$ | Cl | 164–167 |
| $CH_3$ | Cl | H | Cl | 100–103 |
| $CH_3$ | $CH_3$ | H | Cl | 93–94 |
| $CH_3$ | $CH_3$ | $NO_2$ | Cl | 159–160 |
| $NO_2$ | $CH_3$ | H | Cl | 130–131 |

The 2-benzoyl-3-cyclopropylamino-acrylates were converted into the following ethyl 1-cyclopropyl-1,4-dihydro-4-oxo-3-quinolinecarboxylates analogously to Example 1:

TABLE 3

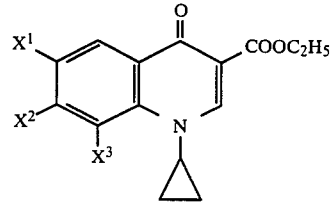

| $X^1$ | $X^2$ | $X^3$ | Melting point (°C.) |
|---|---|---|---|
| Cl | $CH_3$ | H | 218–220 |
| Br | $CH_3$ | H | 191–196 |
| Cl | $CH_3$ | F | 180–185 |
| F | $CH_3$ | Cl | 126–130 |
| F | Cl | $CH_3$ | 170–175 |
| F | $CH_3$ | $NO_2$ | 157–158 |
| $NO_2$ | $CH_3$ | $NO_2$ | 232–233 |
| $CH_3$ | $NO_2$ | H | 177–178 |
| Cl | $CH_3$ | $NO_2$ | 225–227 |
| H | Cl | $CH_3$ | 151–155 |
| $CH_3$ | Cl | H | 160–162 |
| $CH_3$ | $CH_3$ | H | 158–160 |
| $CH_3$ | $CH_3$ | $NO_2$ | 218–221 |
| $NO_2$ | $CH_3$ | H | 262–263 |

Hydrolysis analogous to Example 1 give the corresponding 1-cyclopropyl-1,4-dihydro-4-oxo-3-quinolinecarboxylic acids:

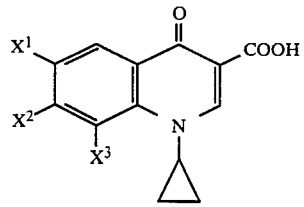

| Example No. | $X^1$ | $X^2$ | $X^3$ | Melting point (°C.) |
|---|---|---|---|---|
| 3 | Cl | $CH_3$ | H | 260–262 |
| 4 | Br | $CH_3$ | H | 280–283 |

-continued

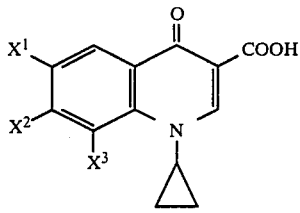

| Example No. | $X^1$ | $X^2$ | $X^3$ | Melting point (°C.) |
|---|---|---|---|---|
| 5 | Cl | $CH_3$ | F | 215–217 |
| 6 | F | $CH_3$ | Cl | 188–189 |
| 7 | F | Cl | $CH_3$ | 191–195 |
| 8 | F | $CH_3$ | $NO_2$ | 261–263 |
| 9 | $NO_2$ | $CH_3$ | $NO_2$ | 250–252 |
| 10 | $CH_3$ | $NO_2$ | H | 236–238 |
| 11 | Cl | $CH_3$ | $NO_2$ | 263–266 |
| 12 | H | Cl | $CH_3$ | 270–272 |
| 13 | $CH_3$ | Cl | H | 248–250 |
| 14 | $CH_3$ | $CH_3$ | H | 280–282 |
| 15 | $CH_3$ | $CH_3$ | $NO_2$ | 271–273 |
| 16 | $NO_2$ | $CH_3$ | H | 264–266 |

The new alkylbenzoic acids used as starting substances were obtained as follows:

Preparation of 2,3-dichloro-5-fluoro-4-methylbenzoic acid 1. 2-Chloro-5-fluoro-4-methylbenzoic acid 41 g of acetyl chloride are added to 200 ml of 1,2-dichloroethane and 80 g of $AlCl_3$ while cooling with ice. 72.3 g of 5-chloro-2-fluorotoluene are then added dropwise. The reaction mixture is warmed at 50° for 8 hours and then poured onto ice. The organic phase is washed with water, dried and distilled. Yield: about 50 g of 2-chloro-5-fluoro-4-methylacetophenone, boiling point$_{10}$: 120°–127°.

A solution of 37.2 g of 2-chloro-5-fluoro-4-methylacetophenone in 280 ml of dioxane is added dropwise at 0° C. to a NaOBr solution prepared from 80 g of NaOH and 96 g of bromine in 400 ml of water. When the reaction has ended, the bromoform is removed. 20 g of $Na_2S_2O_5$ are added to the aqueous phase, which is then acidified with concentrated HCl. 29.1 g of 2-chloro-5-fluoro-4-methylbenzoic acid thereby precipitate. Melting point: 176°–77°.

2. 2-Chloro-5-fluoro-4-methyl-3-nitro-benzoic acid 20 g of 2-chloro-5-fluoro-4-methylbenzoic acid are initially introduced into 60 ml of concentrated $H_2SO_4$. 12.3 g of $KNO_3$ are added in portions, while cooling with ice. The mixture is then warmed to 50° for 2 hours and subsequently poured onto ice. After isolation and recrystallization from toluene, 18.8 g of 2-chloro-5-fluoro-4-methyl-3-nitrobenzoic acid of melting point 186°–88° are obtained.

3. 3-Amino-2-chloro-5-fluoro-4-methyl-benzoic acid 18.5 g of 2-chloro-5-fluoro-4-methyl-3-nitro-benzoic acid and 51.5 g of $Na_2S_2O_4$ are boiled in a mixture of 160 ml of glycol monomethyl ether and 160 g of water for 3 hours. 230 ml of ½-concentrated HCl are added to the still warm solution. The mixture is boiled up once more, cooled and poured into 560 ml of water. The solid which has precipitated is isolated and dried. Yield: 12.4 g, melting point: 182°–84°.

4. Methyl 3-amino-2-chloro-5-fluoro-4-methyl-benzoate 12 g of 3-amino-2-chloro-5-fluoro-4-methylbenzoic acid are initially introduced into 60 ml of MeOH. HCl gas is passed in for 20 minutes and is then boiled under reflux for 5 hours. Thereafter, the mixture is poured into water and rendered alkaline with sodium carbonate and the product is isolated. Yield: 8 g, melting point: 51°–52°.

5. 2,3-Dichloro-5-fluoro-4-methylbenzoic acid 8 g of methyl 3-amino-2-chloro-5-fluoro-4-methyl-benzoate are diazotized with $NaNO_2$/HCl in aqueous solution. This diazonium salt solution is added dropwise to a solution of 4.1 g of CuCl in 16 ml of concentrated HCl. The mixture is then warmed until no further gas is formed. After cooling, the solid which has precipitated is separated off and taken up in 30 ml of 50% strength EtOH. After addition of 2.3 g of NaOH, the mixture is boiled for 1 hour. After cooling to room temperature, the mixture is acidified with HCl and the solid which has precipitated is isolated. Melting point: 179°–80°. Yield: 5.2 g.

Preparation of 2-chloro-4,5-dimethyl-3-nitro-benzoic acid 31.6 g of 2-chloro-4,5-dimethylbenzoic acid are initially introduced into 94 ml of $H_2SO_4$. 19 g of $KNO_3$ are added in portions, while cooling with ice. The mixture is subsequently warmed to 50° for a further 2 hours and then poured onto ice. The product is isolated and recrystallized from toluene. Yield: 25.3 g, melting point: 160°–63°.

Preparation of 2,4-dichloro-5-fluoro-3-methylbenzoic acid 1. 2,4-Dichloro-3-methyl-5-nitrobenzoic acid 30 g of 2,4-dichloro-3-methylbenzoic acid are initially introduced into 83 ml of concentrated $H_2SO_4$. 16.7 g of $KNO_3$ are added in portions, while cooling with ice. The mixture is subsequently warmed at 50° for a further 2 hours and then poured onto ice. The nitro compound is isolated and recrystallized from toluene. Melting point: 152°–4°, yield: 24 g.

2. 5-Amino-2,4-dichloro-3-methylbenzoic acid 55 g of 2,4-dichloro-3-methyl-5-nitrobenzoic acid and 141.6 g of $Na_2S_2O_4$ are boiled in a mixture of 440 ml of glycol monomethyl ether and 440 ml of water for 3 hours. 620 ml of ½-concentrated HCl are added to the still warm solution and the mixture is then boiled up once more. After cooling to room temperature, the mixture is poured into 1.5 l of water and brought to pH 5 with sodium carbonate. 24.6 g of aminobenzoic acid are obtained. Melting point: 202°–3°.

3. Methyl 5-amino-2,4-dichloro-3-methylbenzoate 24 g of 5-amino-2,4-dichloro-3-methylbenzoic acid are initially introduced into 110 ml of methanol. HCl gas is passed in for 20 minutes and the mixture is then boiled under reflux for 5 hours. Thereafter, it is poured into water and rendered alkaline with sodium carbonate. 24 g of ester of melting point 86°–88° are obtained.

4. 2,4-Dichloro-5-fluoro-3-methylbenzoic acid 24 g of methyl 5-amino-2,4-dichloro-3-methylbenzoate are diazotised with $NaNO_2$/HCl in aqueous solution. 26 ml of 30% strength aqueous HBF$_4$ solution are added to the diazonium salt solution at 0° C. The reaction mixture is kept at 0° for 30 minutes. The tetrafluoroborate is then isolated and dried over P$_2$O$_5$. Yield: 23.5 g.

The dried tetrafluoroborate is decomposed under dry conditions in a flask. When the reaction has ended, 100 ml of 50% strength EtOH and 7.9 g of KOH are added to the liquid residue and the mixture is boiled for 1 hour. After cooling, the mixture is rendered acid with HCl and the solid is isolated. After stirring with ligroin, 14.3 g of product of melting point 145°–49° are obtained.

Synthesis of 2,5-dichloro-3-fluoro-4-methylbenzoic acid 1. 2,5-Dichloro-4-methyl-3-nitrobenzoic acid 41 g of 2,5-dichloro-4-methylbenzoic acid are added in portions to a mixture of 100 ml of concentrated H$_2$SO$_4$ and 20 ml of 68% strength HNO$_3$. The mixture is kept at 50° for 3 hours and then poured onto 600 g of ice. The solid which has precipitated is isolated, dried and stirred with a little toluene. Melting point: 210°–18°, yield: 43.8 g.

2. 3-Amino-2,5-dichloro-4-methylbenzoic acid 43 g of 2,5-dichloro-4-methyl-3-nitrobenzoic acid and 108.8 g of Na$_2$S$_2$O$_4$ are boiled in a mixture of 340 ml of glycol monomethyl ether and 340 ml of water for 3 hours. 480 ml of ½-concentrated HCl are added to the still warm solution and the mixture is then boiled up once again. After cooling to room temperature, the mixture is poured into 1 l of ice-water and the strongly acid solution is buffered with Na$_2$CO$_3$ (pH 5). The solid which has precipitated is isolated and dried. Melting point: 218°–21°, yield: 32.5 g.

3. Methyl 3-amino-2,5-dichloro-4-methylbenzoate 30 g of 3-amino-2,5-dichloro-4-methylbenzoic acid are initially introduced into 140 ml of MeOH. HCl gas is now passed in for 20 minutes and the mixture is then boiled under reflux for a further 5 hours. After cooling, the mixture is poured into water and rendered alkaline with sodium carbonate. The ester which has precipitated is isolated and dried. Yield: 30.8 g, melting point: 53°–55°.

4. 2,5-Dichloro-3-fluoro-4-methylbenzoic acid 30 g of methyl 3-amino-2,5-dichloro-4-methylbenzoate are converted into the diazonium salt with NaNO$_2$/HCl in aqueous solution. 33 ml of 30% strength HBF$_4$ are added to the diazonium salt solution at 0° C. After 30 minutes at 0° C., the solid which has formed is isolated, washed with 5% strength HBF$_4$ solution and dried over P$_2$O$_5$.

The diazonium salt is heated under dry conditions in a glass flask. When the reaction has ended, the crude methyl 2,5-dichloro-3-fluoro-4-methylbenzoate is taken up in 100 ml of 50% strength EtOH, and 8.2 g of KOH are added. The mixture is boiled under reflux for 1 hour and, after cooling to room temperature, is acidified with HCl. The benzoic acid which has precipitated is isolated, dried and recrystallized from toluene. Yield: 11.3 g, melting point 195°–6°.

Preparation of 3,5-difluoro-4-methyl-benzoyl chloride 520 g of 3-fluoro-4-methyl-5-nitro-benzoic acid are hydrogenated in 3,500 ml of dioxane with 50 g of Pd-C catalyst (5% strength) at 50° C. and under 30 bar. The catalyst is then filtered off with suction and the solution is concentrated. 403 g of 3-fluoro-4-methyl-5-aminobenzoic acid are obtained as crude material.

The crude material is introduced into 950 ml of anhydrous hydrofluoric acid at 0°–20° C. 196 g of sodium nitrite are then added in portions at 0°–5° C. The mixture is subsequently stirred at 0° C. for 30 minutes, 500 ml of dimethylsulphoxide is allowed to run in and the mixture is subsequently heated slowly, splitting off of nitrogen starting at about 30° C. The mixture is subsequently stirred at 80°–85° C. until the splitting off of N$_2$ has ended. The batch is cooled and poured onto ice and the crystals are filtered off with suction. After dissolving the dilute NaOH, the insoluble portion is filtered off and the solution is again rendered acid with hydrochloric acid. The crystals which have precipitated are filtered off with suction, washed and dried. 293 g of 3,5-difluoro-4-methyl-benzoic acid are obtained as crude material. After addition of 380 ml of thionyl chloride, the mixture is slowly heated to the reflux temperature and stirred until the evolution of gas has ended. The excess thionyl chloride is distilled off, the residue is coarsely distilled over and the distillate is fractionated. 137 g of 3,5-difluoro-4-methylbenzoyl chloride of boiling point: 87°–88° C./18 mbar, n$_D^{20}$: 1.5132 are obtained.

Hydrolysis of a sample gives the free 3,5-difluoro-4-methyl-benzoic acid as crystals of melting point m.p.: 153° C.

Preparation of 3,5-difluoro-4-methyl-6-chloro-benzoyl chloride 30 g of chlorine are passed into 70 g of 3,5-difluoro-4-methyl-benzoyl chloride and a spatula-tip of FeS and I$_2$ at 40°–45°, with slight cooling. The mixture is then flushed with nitrogen, the residue is coarsely distilled and the distillate is fractionated. 44 g of 3,5-difluoro-4-methyl-6-chlorobenzoyl chloride of boiling point: 109°/16 mbar, n$_D^{20}$: 1.5342 are obtained. 3,5-Difluoro-2,6-dichloro-4-methyl-benzoyl chloride of boiling point b.p: 109°/13 mbar, n$_D^{20}$: 1.5274 are obtained from the last runnings.

Preparation of 2-nitro-4-methyl-5-fluoro-benzoic acid 50 g of 3-fluoro-4-methyl-benzoic acid are initially introduced into 100 ml of concentrated sulphuric acid, and a mixture consisting of 26 g of 98% strength nitric acid and 40 g of concentrated sulphuric acid is added dropwise at 20°–25°, while cooling with ice. The mixture is subsequently stirred at room temperature for 1 hour. The batch is then poured onto ice-water and the crystals are filtered off with suction and washed thoroughly with water. After drying and recrystallization from toluene, 48 g (74.3% of theory) of 2-nitro-4-methyl-5-fluorobenzoic acid of melting point m.p.: 163°–5° C. are obtained.

Preparation of 2-amino-4-methyl-5-fluoro-benzoic acid 525 g of 2-nitro-4-methyl-5-fluoro-benzoic acid are hydrogenated in 3 l of dioxane with 50 g of 5% strength Pd-C catalyst at 30°–40° under 20–30 bar. The catalyst is filtered off with suction and the solution is poured onto water. The crystals which have precipitated are filtered off with suction and dried. Yield: 357 g (80.1% of theory), melting point: 201°–202° C.

Preparation of 2,5-difluoro-4-methyl-benzoic acid 850 ml of anhydrous hydrofluoric acid are taken and 352 g of 2-amino-4-methyl-5-fluoro-benzoic acid are introduced at 0°-20° C. 173 g of sodium nitrite are then introduced in portions at 0°-5° C. in the course of about 60 minutes. The mixture is subsequently stirred at 0° C. for 1 hour and is then slowly heated to 40°. 850 ml of dimethylsulphoxide are added dropwise and heating is continued. At 90°-100°, the mixture is stirred until the splitting off of nitrogen has ended, and is then cooled and poured onto ice. The crystals are filtered off with suction and dried. Yield: 250 g, melting point: 152°-8° C.

From toluene: 162 g, 2,5-difluoro-4-methyl-benzoic acid of melting point m.p.: 160° C.

Preparation of 2,5-difluoro-4-methyl-benzoyl chloride 250 ml of thionyl chloride are taken and 120 g of 2,5-difluoro-4-methyl-benzoic acid are introduced in portions at room temperature, with brisk evolution of gas. When the evolution of gas has subsided, the mixture is heated slowly to the reflux temperature and stirred until the evolution of gas has ended. The excess thionyl chloride is distilled off, the reaction product is coarsely distilled over and the distillate is fractionated on a small column. Yield: 97 g (72.9% of theory) of 2,5-difluoro-4-methylbenzoyl chloride of boiling point b.p.: 103°/20 mbar, $n_D^{20}$: 1.5232.

It is understood that the specification and examples are illustrative but not limitative of the present invention and that other embodiments within the spirit and scope of the invention will suggest themselves to those skilled in the art.

We claim:

1. An alkyl-1-cyclopropyl-1,4-dihydro-4-oxo-3-quinolinecarboxylic acid of the formula

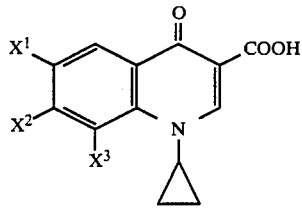

in which
$X^1$ is hydrogen, a nitro group or a halogen atom, and
$X^2$ and $X^3$ each independently is hydrogen, a nitro group, a halogen atom or an alkyl radical with 1 to 3 carbon atoms, with the proviso that at least one of them is an alkyl radical,
or a pharmaceutically acceptable salt or hydrate thereof.

2. An alkyl-1-cyclopropyl-1,4-dihydro-4-oxo-3-quinolinecarboxylic acid according to claim 1, selected from the group consisting of 1-cyclopropyl-6,8-difluoro-7-methyl-1,4-dihydro-4-oxo-3-quinolinecarboxylic acid, 1-cyclopropyl-6-fluoro-7-methyl-1,4-dihydro-4-oxo-3-quinolinecarboxylic acid, 1-cyclopropyl-6-chloro-7-methyl-1,4-dihydro-4-oxo-3-quinolinecarboxylic acid, 7-chloro-1-cyclopropyl-8-methyl-1,4-dihydro-4-oxo-3-quinolinecarboxylic acid, 8-chloro-1-cyclopropyl-6-fluoro-7-methyl-1,4-dihydro-4-oxo-3-quinolinecarboxylic acid, 6-chloro-1-cyclopropyl-8-fluoro-7-methyl-1,4-dihydro-4-oxo-3-quinolinecarboxylic acid, 7-chloro-1-cyclopropyl-6-fluoro-8-methyl-1,4-dihydro-4-oxo-3-quinolinecarboxylic acid, 1-cyclopropyl-6-fluoro-7-methyl-8-nitro-1,4-dihydro-4-oxo-3-quinolinecarboxylic acid, 1-cyclopropyl-7-methyl-6,8-dinitro-1,4-dihydro-4-oxo-3-quinolinecarboxylic acid, 6-chloro-1-cyclopropyl-7-methyl-8-nitro-1,4-dihydro-4-oxo-3-quinolinecarboxylic acid, and 1-cyclopropyl-7-methyl-6-nitro-1,4-dihydro-4-oxo-3-quinolinecarboxylic acid and a pharmaceutically acceptable alkali metal salt, alkaline earth metal salt and hydrate thereof.

3. A compound according to claim 1, wherein such compound is 1-cyclopropyl-6,8-difluoro-7-methyl-1,4-dihydro-4-oxo-3-quinolinecarboxylic acid of the formula

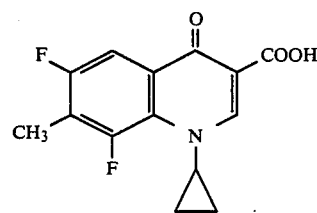

or a pharmaceutically acceptable salt or hydrate thereof.

4. A compound according to claim 1, wherein such compound is 1-cyclopropyl-6-fluoro-7-methyl-1,4-dihydro-4-oxo-3-quinolinecarboxylic acid of the formula

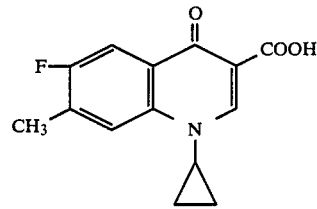

or a pharmaceutically acceptable salt or hydrate thereof.

5. A compound according to claim 1, wherein such compound is 8-chloro-1-cyclopropyl-6fluoro-7-methyl-1,4-dihydro-4-oxo-3-quinolinecarboxylic acid of the formula

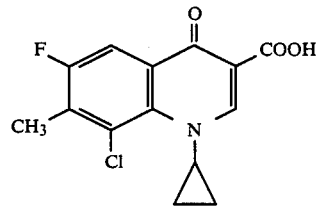

or a pharmaceutically acceptable salt or hydrate thereof.

6. A compound according to claim 1, wherein such compound is 7-chloro-1-cyclopropyl-6-fluoro-8-methyl-1,4-dihydro-4-oxo-3-quinolinecarboxylic acid of the formula

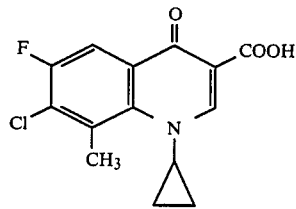

or a pharmaceutically acceptable salt or hydrate thereof.

7. A compound according to claim 1, wherein such compound is 7-chloro-1-cyclopropyl-8-methyl-1,4-dihydro-4-oxo-3-quinolinecarboxylic acid of the formula

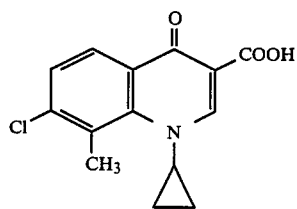

or a pharmaceutically acceptable salt or hydrate thereof.

8. An antibacterial or animal growth-promoting composition comprising an amount effective therefor of a compound salt or hydrate according to claim 1 in admixture with a diluent.

9. A unit dose of a composition according to claim 8 in the form of a tablet, capsule or ampule.

10. A method of combating bacteria which comprises applying to such bacteria or to a bacteria host an antibacterially effective amount of a compound, salt or hydrate according to claim 1.

11. The method according to claim 10 wherein said compound is
1-cyclopropyl-6,8-difluoro-7-methyl-1,4-dihydro-4-oxo-3-quinolinecarboxylic acid,
1-cyclopropyl-6-fluoro-7-methyl-1,4-dihydro-4-oxo-3-quinolinecarboxylic acid,
8-chloro-1-cyclopropyl-6-fluoro-7-methyl-1,4-dihydro-4-oxo-3-quinolinecarboxylic acid,
7-chloro-1-cyclopropyl-6-fluoro-8-methyl-1,4-dihydro-4-oxo-3-quinolinecarboxylic acid or
7-chloro-1-cyclopropyl-8-methyl-1,4-dihydro-4-oxo-3-quinolinecarboxylic acid,
or a pharmaceutically acceptable salt thereof.

12. A method of promoting the growth of animals which comprises administering to such animals an amount effective therefor of a compound, salt or hydrate according to claim 1.

13. The method according to claim 12 wherein said compound is
1-cyclopropyl-6,8-difluoro-7-methyl-1,4-dihydro-4-oxo-3-quinolinecarboxylic acid,
1-cyclopropyl-6-fluoro-7-methyl-1,4-dihydro-4-oxo-3-quinolinecarboxylic acid,
8-chloro-1-cyclopropyl-6-fluoro-7-methyl-1,4-dihydro-4-oxo-3-quinolinecarboxylic acid,
7-chloro-1-cyclopropyl-6-fluoro-8-methyl-1,4-dihydro-4-oxo-3-quinolinecarboxylic acid or
7-chloro-1-cyclopropyl-8-methyl-1,4-dihydro-4-oxo-3-quinolinecarboxylic acid,
or a pharmaceutically acceptable salt thereof.

* * * * *